United States Patent [19]

VandenBerg

[11] Patent Number: Plant 6,332

[45] Date of Patent: Oct. 11, 1988

[54] CHRYSANTHEMUM PLANT NAMED DARK CIRCUS

[75] Inventor: Cornelis P. VandenBerg, Salinas, Calif.

[73] Assignee: Yoder Brothers, Inc., Barberton, Ohio

[21] Appl. No.: 931,866

[22] Filed: Nov. 18, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Dark Circus particularly characterized by its flat capitulum form; daisy capitulum type; red-purple ray floret color; diameter across face of capitulum of up to 6.5 cm at maturity when grown as a pinched spray pot mum; uniform nine week photoperiodic flowering response to short days; medium plant height when grown as a pinched pot mum; and by its semi-spreading branching pattern.

3 Drawing Sheets

The present invention comprises a new and distinct cultivar of chrysanthemum, botanically known as *Chrysanthemum morifolium,* Ramat., and referred to by the cultivar name Dark Circus.

Dark Circus, identified as 72261N02, is a product of a mutation induction program which had the objective of creating new chrysanthemum cultivars that would expand the color range of an existing cultivar while retaining all other traits.

Dark Circus was discovered and selected by Cornelis P. VandenBerg on Oct. 13, 1983 in a controlled environment in Salinas, Calif. as one flowering plant within a flowering block established as rooted cuttings from stock plants which had been exposed as unrooted cuttings to an x-ray source of 1750 rads. The irradiated parent was the cultivar identified as Circus, disclosed in U.S. Plant Pat. No. 4,188.

The first act of asexual reproduction of Dark Circus was accomplished when vegetative cuttings were taken from the initial selection in December 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dark Circus are firmly fixed and are retained through successive generations of asexual reproduction.

Dark Circus has not been observed under all possible environmental conditions. The phenotype may vary significantly with variations in environment such as temperature, light intensity, and day length.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Dark Circus, which, in combination, distinguish this chrysanthemum as a new and distinct cultivar:

1. Flat capitulum form.
2. Daisy capitulum type.
3. Red-purple ray floret color.
4. Diameter across face of capitulum up to 6.5 cm at maturity, when grown as a pinched spray pot mum.

5. Uniform nine week photoperiodic flowering response to short days.
6. Medium plant height, requiring 0 to 7 long days after pinch prior to short days and 1 application of 2500 ppm B-9 SP to attain a flowered plant height of 25 to 35 cm for year round flowerings when grown as a pinched pot mum.
7. Semi-spreading branching pattern.

The accompanying photographic drawings show typical inflorescence and leaf characteristics of Dark Circus, with the colors being as nearly true as possible with illustrations of this type. Sheet 1 is a color photograph of Dark Circus grown as a pinched spray pot mum. Sheet 2 is a black and white photograph of three views of the inflorescence of Dark Circus. Sheet 3 is a black and white photograph showing the upper and under sides of the leaves of Dark Circus at three stages of development (mature, intermediate and immature).

Of the commercial cultivars known to the inventor, the most similar in comparison to Dark Circus is the parent cultivar Circus. All traits of Dark Circus are similar to those of Circus, except the color of ray florets and the diameter across face of capitulum. The color of the ray florets of Dark Circus is red-purple, as contrasted with the lavender-pink ray florets of Circus. The diameter across face of capitulum of Dark Circus is up to 6.5 cm at maturity, with the capitulum diameter of Circus being up to 7.0 cm at maturity.

In the following description, color references are made to The Royal Horticultural Society Colour Chart. The color values were determined on plant material grown as a pinched spray pot mum in Salinas, Calif. on Mar. 24, 1986.

Classification:

*Botanical.*—*Chrysanthemum morifolium,* Ramat., cv. Dark Circus.

*Commercial.*—Daisy spray pot mum.

INFLORESCENCE

A. Capitulum:

*Form.*—Flat.

*Type.*—Daisy.

*Diameter across face.*—Up to 6.5 cm at maturity.

B. Corolla of ray florets:

*Color (general tonality from a distance of three meters).*—Red-purple.

*Color (upper surface).*—70B.

*Color (under surface).*—74B to 74C.

*Shape.*—Flat, oblong.

C. Corolla of disc florets:

*Color (mature).*—14A to 14B.

*Color (immature).*—144B to 144C.

D. Reproductive organs:

*Androecium.*—Present on disc florets only; moderate pollen.

*Gynoecium.*—Present on both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

*Branching patern.*—Semi-spreading.

B. Foliage:

*Color (upper surface).*—147A to 147B.

*Color (under surface).*—148B.

*Shape.*—Lobed and serrated.

I claim:

1. A new and distinct chrysanthemum plant named Dark Circus, as described and illustrated, and particularly characterized as to uniqueness by the combined characteristics of flat capitulum form; daisy capitulum type; red-purple ray floret color; diameter across face of capitulum of up to 6.5 cm at maturity when grown as a pinched spray pot mum; uniform nine week photoperiodic flowering response to short days; medium plant height when grown as a pinched pot mum; and semi-spreading branching pattern.

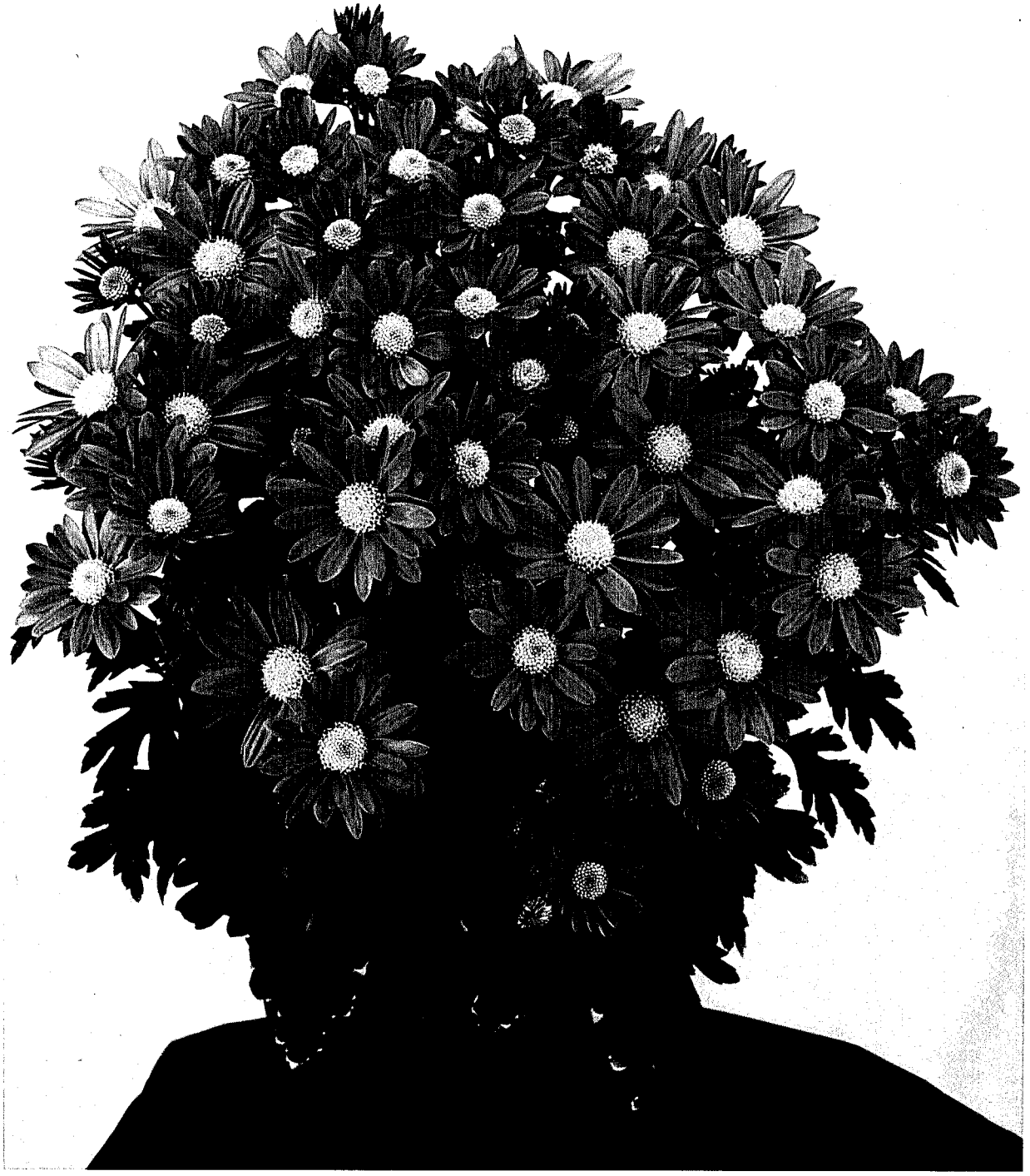

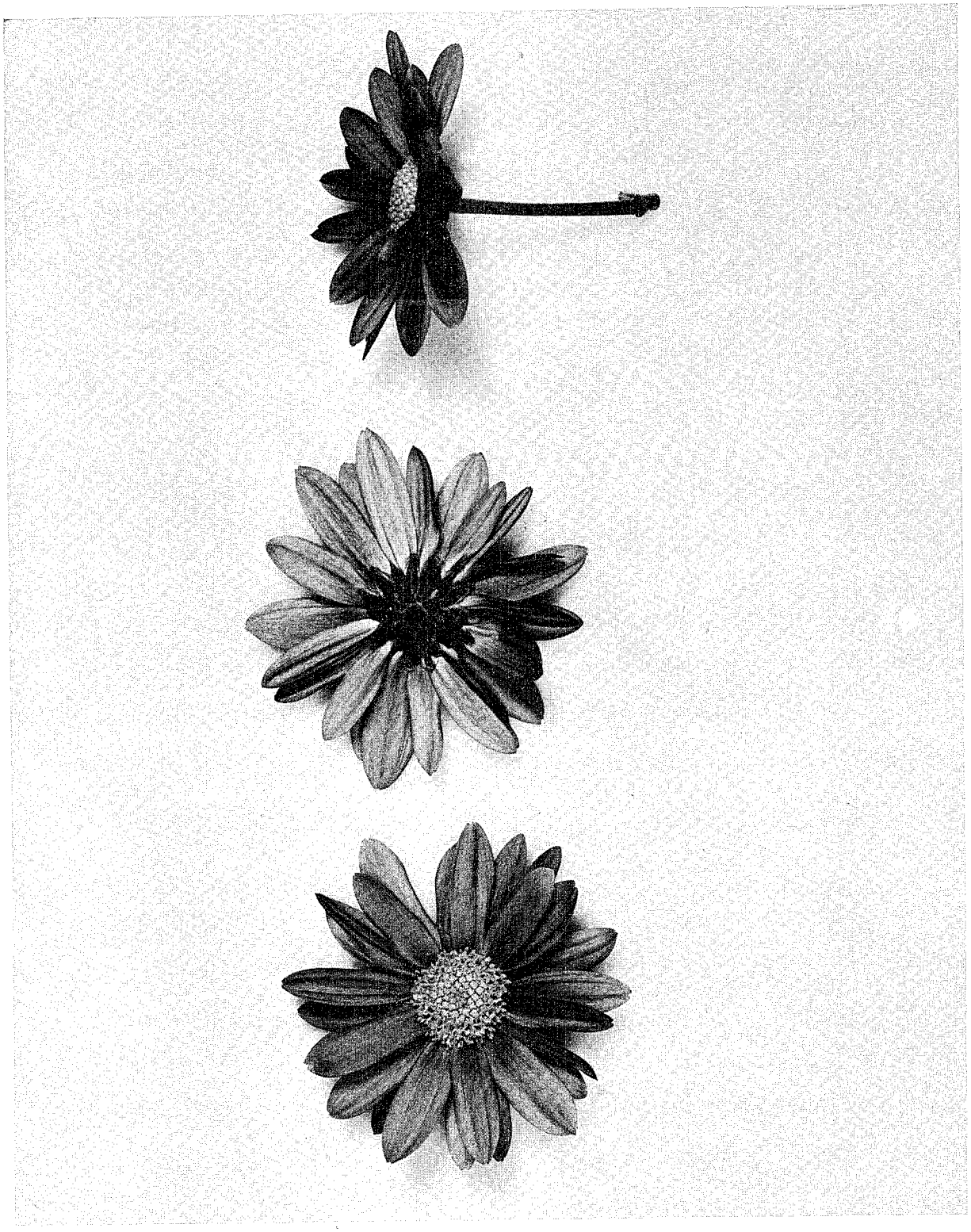

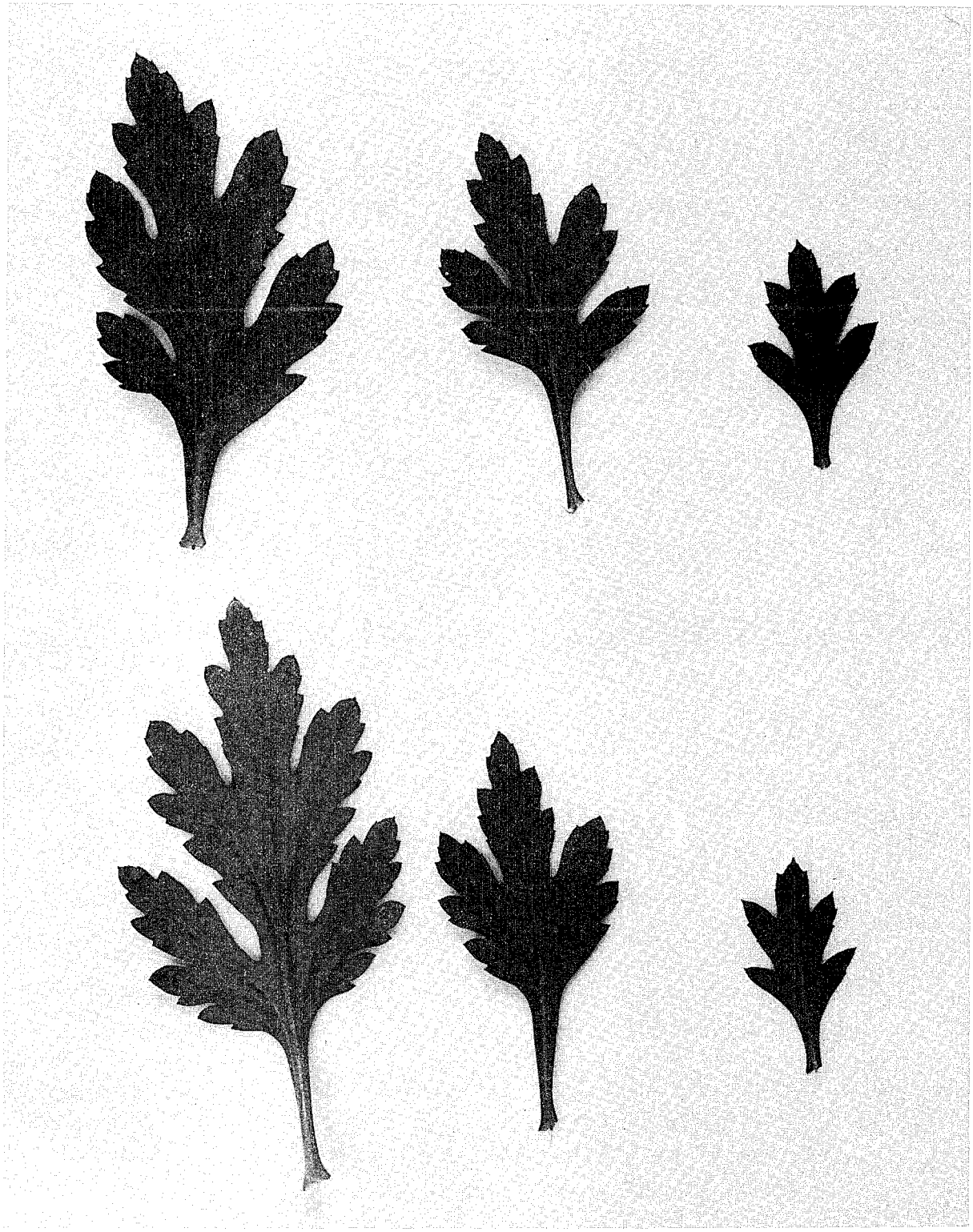

* * * * *